United States Patent [19]

Kanoo et al.

[11] Patent Number: 4,965,261
[45] Date of Patent: Oct. 23, 1990

[54] SUBSTITUTED BENZOXAZINORIFAMYCIN DERIVATIVE AND ANTIBACTERIAL AGENT CONTAINING THE SAME

[75] Inventors: Fumihiko Kanoo, Takasago; Takehiko Yamane, Akashi; Hideo Kondo; Takuji Hashizume, both of Takasago; Katsuji Yamashita, Kobe; Kazunori Hosoe, Takasago; Fumiyuki Kuze, Kyoto; Kiyoshi Watanabe, Akashi, all of Japan

[73] Assignee: Kanegafuchi Kagaku Kogyo Kabushiki Kaisha, Osaka, Japan

[21] Appl. No.: 324,499

[22] Filed: Mar. 16, 1989

[30] Foreign Application Priority Data

Mar. 18, 1988 [JP] Japan .................................. 63-67014
Sep. 24, 1988 [JP] Japan ................................. 63-239288

[51] Int. Cl.$^5$ .................. A61K 31/535; C07D 521/00
[52] U.S. Cl. .................................. 514/229.5; 514/183; 540/457
[58] Field of Search .............. 540/457; 514/183, 229.5

[56] References Cited

U.S. PATENT DOCUMENTS 4,005,077  1/1977  Bickel et al. ......................... 540/459
4,690,919  9/1987  Yamane et al. ....................... 514/183
4,859,661  8/1989  Kano et al. ........................... 514/183

Primary Examiner—Glennon H. Hollrah
Assistant Examiner—James H. Turnipseed
Attorney, Agent, or Firm—Armstrong, Nikaido, Marmelstein, Kubovcik & Murray

[57] ABSTRACT

A rifamycin derivative having the formula (I):

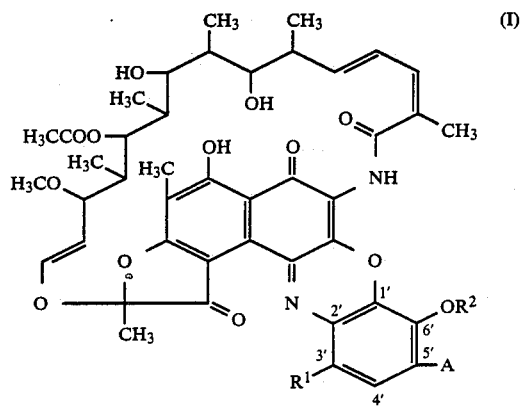

wherein $R^1$ is hydrogen atom, methyl group or ethyl group, $R^2$ is an alkyl group having 1 to 4 carbon atoms, and A is a group having the formula:

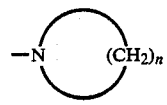

in which n is an integer of 3 to 5, or group having the formula:

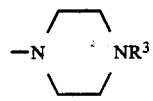

in which $R^3$ is a alkyl group having 1 to 5 carbon atoms; or a salt thereof. The rifamycin derivative (I) exhibits a strong antibacterial activity against Gram-positive bacteria and acid-fast bacteria, and also exhibits a strong antibacterial activity against tubercle bacilli.

7 Claims, 1 Drawing Sheet

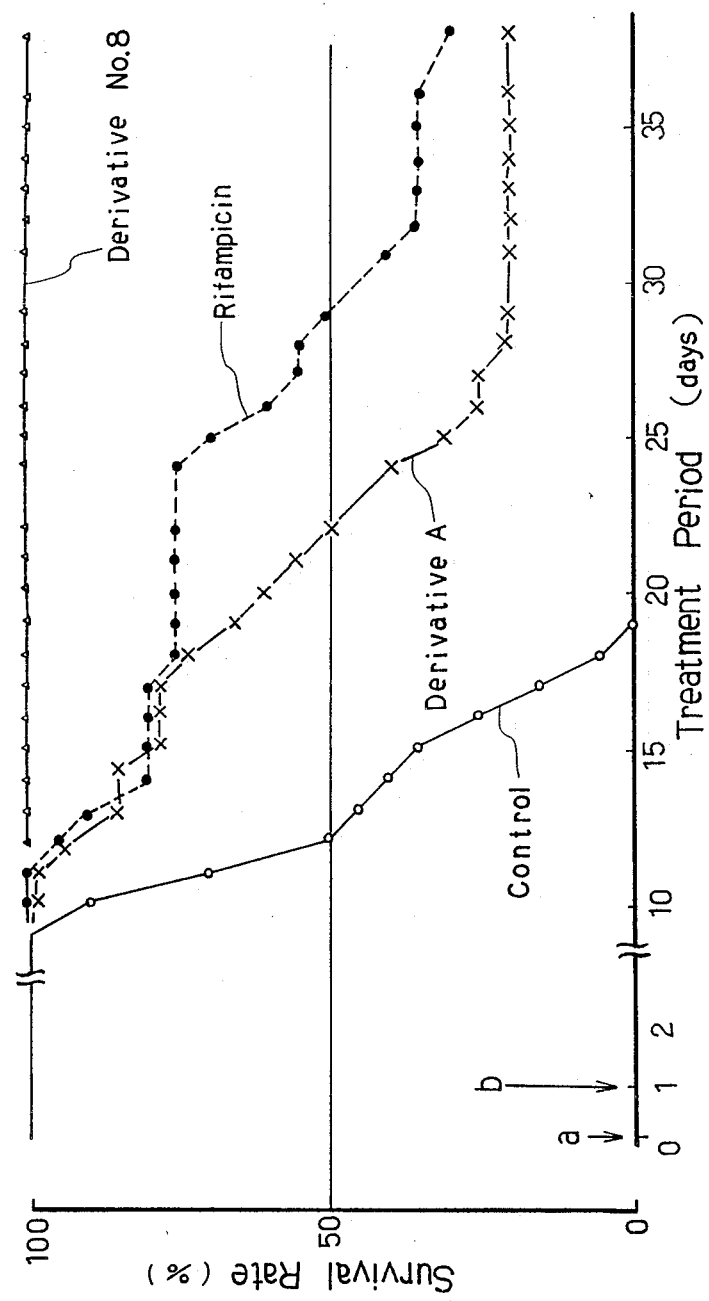

SUBSTITUTED BENZOXAZINORIFAMYCIN DERIVATIVE AND ANTIBACTERIAL AGENT CONTAINING THE SAME

BACKGROUND OF THE INVENTION

The present invention relates to a novel rifamycin derivative or salts thereof, a process for preparing the same and antibacterial agents containing the same as an effective component. More particularly, the present invention relates to a novel rifamycin derivative having the formula (I):

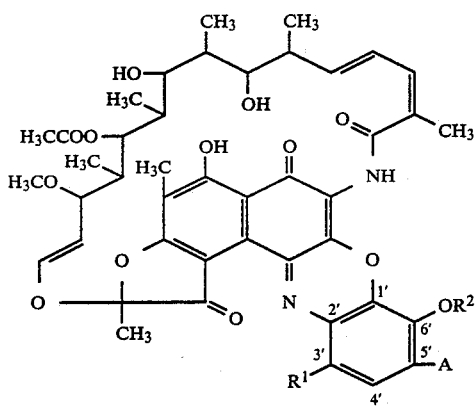

wherein $R^1$ is hydrogen atom, methyl group or ethyl group, $R^2$ is an alkyl group having 1 to 4 carbon atoms, and A is a group having the formula:

in which n is an integer of 3 to 5, or a group having the formula:

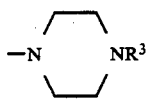

in which $R^3$ is an alkyl group having 1 to 5 carbon atoms, or salts thereof, a process for preparing the same and antibacterial agents containing the same as an effective ingredient.

The rifamycin derivative of the present invention is a novel compound which has not yet been reported in the literature.

For the purpose of developing a novel superior antibacterial agent, the present inventors have synthesized a novel rifamycin derivative having the formula (I):

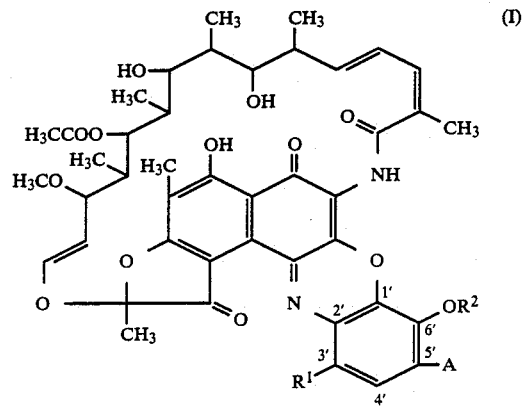

wherein $R^1$, $R^2$ and A are as defined above and investigated the antibacterial activity and pharmacological characteristics thereof, and as a result, found that the novel rifamycin derivative having the formula (I) exhibits a strong antibacterial activity and excellent pharmacological characteristics.

SUMMARY OF THE INVENTION

The present invention provides a rifamycin derivative having the formula (I):

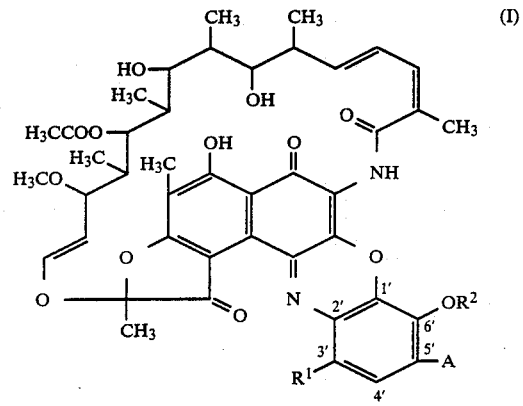

wherein $R^1$ is hydrogen atom, methyl group or ethyl group, $R^2$ is an alkyl group having 1 to 4 carbon atoms, and A is a group having the formula:

in which n is an integer of 3 to 5, or a group having the formula:

in which $R^3$ is an alkyl group having 1 to 5 carbon atoms; or a salt thereof.

Further, the present invention provides a process for preparing the rifamycin derivative having the formula (I), which comprises reacting a rifamycin derivative having the formula (II):

<p>(structure II shown at top of page)</p> wherein R[1] is hydrogen atom, methyl group or ethyl group, R[2] is an alkyl group having 1 to 4 carbon atoms, and X is hydrogen atom, an alkoxyl group having 1 to 6 carbon atoms, a halogen atom or nitro group, with an amine having the formula:

A—H wherein A is a group having the formula:

$$-N\underset{}{\overset{}{\frown}}(CH_2)_n$$

in which n is an integer of 3 to 5 or a group having the formula:

$$-N\underset{\diagdown\_\_\diagup}{\overset{\diagup\phantom{x}\diagdown}{\phantom{x}}}NR^3$$

in which R[3] is an alkyl group having 1 to 5 carbon atoms.

Still further, the present invention provides an antibacterial composition comprising the rifamycin derivative having the formula (I) or a pharmacologically acceptable salt thereof as an effective ingredient.

BRIEF EXPLANATION OF THE DRAWING

FIG. 1 is a graph showing relationships between the survival rate of mice and the treatment period in tests wherein the rifamycin derivative of the invention or other test compounds were orally administered to mice suffering from tuberculosis.

DETAILED DESCRIPTION

The rifamycin derivative having the formula (I) according to the present invention is soluble in various kinds of organic solvents, e.g. halogenated hydrocarbons such as chloroform, alcohols such as ethanol, esters such as ethyl acetate, aromatic hydrocarbons such as benzene, and ethers such as tetrahydrofuran.

Examples of the substituents, R[2], and, A, in the novel rifamycin derivative of the present invention having the formula (I) are as follows:

Examples of R[2] are methyl group, ethyl group, n-propyl group, isopropyl group, n-butyl group, isobutyl group, sec-butyl group and tert-butyl group.

Examples of the group, $$-N\underset{}{\overset{}{\frown}}(CH_2)_n$$

in which n is as defined above, for A are $$-N\underset{\diagdown\diagup}{\overset{\diagup\diagdown}{\phantom{x}}},\ -N\underset{\diagdown\_\diagup}{\overset{\diagup\phantom{x}\diagdown}{\phantom{x}}}\ \text{and}\ -N\underset{\diagdown\_\_\diagup}{\overset{\diagup\phantom{xx}\diagdown}{\phantom{xx}}}.$$

Examples of the group, $$-N\underset{\diagdown\_\_\diagup}{\overset{\diagup\phantom{x}\diagdown}{\phantom{x}}}NR^3$$

a which R[3] is as defined above, for A are, for instance, $$-N\underbrace{\phantom{xxx}}NCH_3,\ -N\underbrace{\phantom{xxx}}NC_2H_5,$$

$$-N\underbrace{\phantom{xxx}}NCH_2CH_2CH_3,\ -N\underbrace{\phantom{xxx}}NCH(CH_3)_2,$$

$$-N\underbrace{\phantom{xxx}}N(CH_2)_3CH_3,\ -N\underbrace{\phantom{xxx}}NCH_2CH(CH_3)_2,$$

and the like.

The rifamycin derivative of the present invention having the formula (I) can form a salt with either a base or an acid. Any base or acid capable of forming a salt with the rifamycin derivative having the formula (I) can be employed. Examples of the salts with bases are (1) metal salts, especially alkali metal salts and alkaline earth metal salts, (2) ammonium salt, and (3) amine salts, especially salts with methylamine, ethylamine, diethylamine, triethylamine, pyrrolidine, morpholine or hexamethyleneimine, or the like. Examples of the salts with acids are (1) salts with mineral acids such as sulfuric acid and hydrochloric acid, and (2) salts with organic acids such as p-toluenesulfonic acid, trifluoroacetic acid and acetic acid.

The rifamycin derivative of the present invention having the formula (I) can be prepared by the following processes:

(A) The rifamycin derivative having the formula (I) can be prepared by reacting rifamycin S with a compound having the formula:

(structure shown: aminophenol with OH, OR², R¹, A substituents)

wherein $R^1$, $R^2$, and A are as defined above, according to the method disclosed by W. Kump et al [Helv. Chim. Acta, 56, 2348 (1973)].

(B) The rifamycin derivative having the formula (I) can be prepared by reacting the rifamycin derivative having the formula (II):

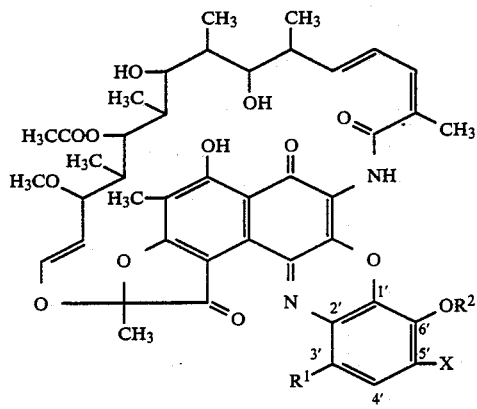

wherein $R^1$ is hydrogen atom, methyl group or ethyl group, $R^2$ is an alkyl group having 1 to 4 carbon atoms, and X is hydrogen atom, an alkoxyl group having 1 to 6 carbon atoms, a halogen atom or a nitro group, dissolved in an organic solvent such as methanol, ethanol, tetrahydrofuran, N,N-dimethylformamide or dimethyl sulfoxide, with an amine having the formula:

A—H wherein A is as defined above, in the presence or absence of an acid such as hydrochloric acid at a temperature ranging from −20° C. to the boiling point of the solvent used for 1 hour to 1 month and in the presence or absence of an oxidizing agent such as manganese dioxide.

In the above reaction, the amine having the formula: A—H wherein A is as defined above, is used in an amount of 0.5 to 10 moles, preferably 1 to 4 moles per 1 mole of the rifamycin derivative having the formula (II), yielding more favorable results.

Examples of the reaction solvent employed in the above process are, for instance, methanol, ethanol, isopropyl alcohol, tetrahydrofuran, pyridine, acetone, ethyl acetate, chloroform, N,N-dimethylformamide, dimethylsulfoxide, and the like. Among them, pyridine, N,N-dimethylformamide and dimethylsulfoxide are preferably employed with more favorable results.

The reaction temperature ranges from −20° C. to the boiling point of the solvent used, and the preferred reaction temperature ranges from −5° C. to 50° C., yielding more favorable results.

The reaction time usually ranges from 1 hour to 1 month. However, the optimum reaction time should be determined by following the progress of the reaction by means of thin layer chromatography or the like since the reaction time varies depending on reaction conditions such as the kind and amount of the amine employed, the presence or absence of an oxidizing agent, the kind and amount the oxidizing agent employed, and the reaction temperature.

When the reaction is carried out in the presence of an oxidizing agent, air, oxygen, manganese dioxide, lead dioxide, silver oxide, potassium ferricyanide, hydrogen peroxide, and the like are employed as the oxidizing agent. Among them, manganese dioxide, silver oxide and potassium ferricyanide are preferably employed with more favorable results.

The rifamycin derivative having the formula (II), which is a starting material in the process of the invention, can be prepared by reacting rifamycin S with a compound represented by the formula:

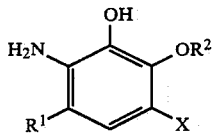

wherein $R^1$, $R^2$ and X are as defined above, according to the method disclosed by W. Kump et al [Helv. Chim. Acta, 56, 2348 (1973)].

The rifamycin derivative of the present invention having the formula (I), can be isolated and purified from the reaction mixture in a relatively easy manner. That is, an excess amount of the amine having the formula: A—H wherein A is as defined above and the reaction solvent, etc, are removed from the reaction mixture to give a crude product, which is then purified by crystallization, column-chromatography or the like. Thus, the desired rifamycin derivative can be obtained.

The rifamycin derivative of the present invention having the formula (I) can be converted into a rifamycin derivative having the formula (III):

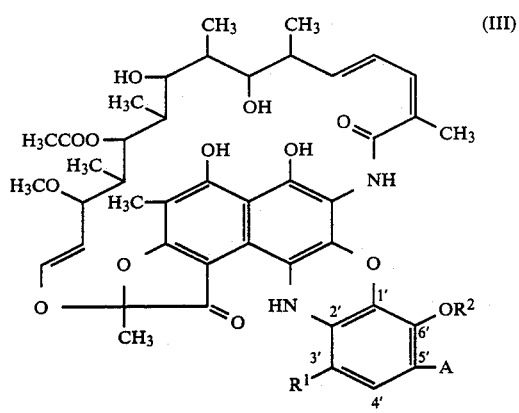

wherein $R^1$, $R^2$ and A are as defined above, by reducing the rifamycin derivative having the formula (I) with a reducing agent such as ascorbic acid or sodium dithionite. The rifamycin derivative having the formula (III) is also a novel compound and possesses a strong antibacterial activity.

Typical examples of the rifamycin derivatives (I) of the present invention are shown in Table 1. The infrared absorption (IR) spectrum was measured according to the potassium bromide tablet method. The thin layer chromatography (TLC) was carried out using silica gel 60 $F_{254}$ plate for thin layer chromatography (20 cm×20 cm, E. Merck Co.). The nuclear magnetic resonance (NMR) spectrum was measured in deuterated chloroform using tetramethylsilane as an internal standard.

TABLE 1

| Derivative No. | R¹ | R² | A | Crystal form | TLC Rf | TLC Solvent system* | IR spectrum (cm⁻¹) | Chemical shift of proton in amino group introduced (δ, ppm)** |
|---|---|---|---|---|---|---|---|---|
| 1 | —H | —CH₃ |  | needle | 0.35 | A | 1,597 (C=O) | 3.70 (CH₂NCH₂, 4H, br) |
| 2 | —H | —CH₃ | 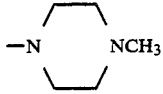 | amorphous | 0.26 | B | 1,598 (C=O) | 2.37 (NCH₃, 3H, s) |
| 3 | —H | —CH₃ | 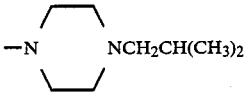 | amorphous | 0.40 | A | 1,598 (C=O) | 0.94 (CH₃, 6H, d) |
| 4 | —H | —C₂H₅ |  | amorphous | 0.37 | A | 1,595 (C=O) | 3.71 (CH₂NCH₂, 4H, br) |
| 5 | —H | —C₂H₅ | 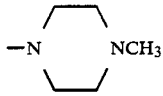 | amorphous | 0.30 | B | 1,594 (C=O) | 2.37 (NCH₃, 3H, s) |
| 6 | —H | —C₂H₅ |  | amorphous | 0.42 | B | 1,598 (C=O) | 1.15 (NCH₂C$\underline{H}$₃, 3H, t) |
| 7 | —H | —C₂H₅ |  | amorphous | 0.23 | B | 1,594 (C=O) | 1.10 (CH₃, 6H, d) |
| 8 | —H | —C₂H₅ |  | amorphous | 0.42 | A | 1,604 (C=O) | 0.96 (CH₃, 6H, d) |
| 9 | —H | —CH₂CH₂CH₃ |  | amorphous | 0.45 | A | 1,594 (C=O) | 3.70 (CH₂NCH₂, 4H, br) |
| 10 | —H | —CH₂CH₂CH₃ | 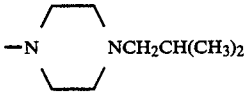 | amorphous | 0.45 | A | 1,604 (C=O) | 0.93 (CH₃, 6H, d) |
| 11 | —H | —CH(CH₃)₂ |  | amorphous | 0.45 | A | 1,592 (C=O) | 3.68 (CH₂NCH₂, 4H, br) |
| 12 | —H | —CH(CH₃)₂ | 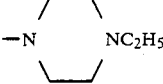 | amorphous | 0.34 | B | 1,600 (C=O) | 1.15 (NCH₂C$\underline{H}$₃, 3H, t) |
| 13 | —H | —CH(CH₃)₂ | 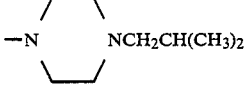 | amorphous | 0.46 | A | 1,594 (C=O) | 0.94 (CH₃, 6H, d) |

TABLE 1-continued

| Derivative No. | R¹ | R² | A | Crystal form | TLC Rf | Solvent system* | IR spectrum (cm$^{-1}$) | Chemical shift of proton in amino group introduced (δ, ppm)** |
|---|---|---|---|---|---|---|---|---|
| 14 | —H | —CH$_2$CH(CH$_3$)$_2$ | —N⟨ ⟩NCH$_2$CH(CH$_3$)$_2$ | amorphous | 0.50 | A | 1,595 (C = O) | 0.94 (CH$_3$, 6H, d) |
| 15 | —CH$_3$ | —CH$_3$ | —N⟨ ⟩ | amorphous | 0.37 | A | 1,597 (C = O) | 3.71 (CH$_2$NCH$_2$, 4H, br) |
| 16 | —CH$_3$ | —CH$_3$ | —N⟨ ⟩NCH$_3$ | amorphous | 0.44 | C | 1,604 (C = O) | 2.37 (NCH$_3$, 3H, s) |
| 17 | —CH$_3$ | —CH$_3$ | —N⟨ ⟩NCH$_2$CH(CH$_3$)$_2$ | needle | 0.41 | A | 1,600 (C = O) | 0.93 (CH$_3$, 6H, d) |

(Notes)
*Solvent system
A: ethyl acetate
B: chloroform/methanol = 95/5 (v/v)
C: chloroform/methanol = 9/1 (v/v)
**Abbreviation
s: singlet, d: doublet, t: triplet, br: broad The rifamycin derivative (I) of the present invention shows a strong antibacterial activity against Gram-positive bacteria and acid-fast bacteria.

The antibacterial activity of the rifamycin derivative (I) of the present invention was determined according to the standard method of Japan Society of Chemotherapy [Chemotherapy (Tokyo), 29, 76 (1981)]. The results obtained with respect to the typical compounds are shown in Table 2. As shown in Table 2, the rifamycin derivative (I) of the present invention shows a strong antibacterial activity against Gram-positive bacteria and acid-fast bacteria. Derivative No. in Table 2 corresponds to derivative No. in Table 1.

TABLE 2

| Test organism | Minimal inhibitory concentration (μg/ml) | | | | |
|---|---|---|---|---|---|
| | Derivative No. 1 | Derivative No. 2 | Derivative No. 3 | Derivative No. 4 | Derivative No. 5 |
| Micrococcus luteus IFO 12708 | 0.04 | 0.02≧ | 0.08 | 0.04 | 0.02≧ |
| Bacillus subtilis IFO 3134 | 0.16 | 0.02≧ | 0.04 | 0.04 | 0.02≧ |
| Staphylococcus aureus IFO 12732 | 0.02≧ | 0.02≧ | 0.02≧ | 0.02≧ | 0.02≧ |
| Escherichia coli IFO 12734 | >10 | 2.5 | >10 | >10 | 2.5 |
| Klebsiella pneumoniae IFO 3512 | >10 | 2.5 | >10 | >10 | 2.5 |
| Mycobacterium smegmatis ATCC 607 | 2.5 | 1.25 | 1.25 | 0.63 | 1.25 |

| Test organism | Minimal inhibitory concentration (μg/ml) | | | | |
|---|---|---|---|---|---|
| | Derivative No. 6 | Derivative No. 7 | Derivative No. 8 | Derivative No. 9 | Derivative No. 10 | Derivative No. 11 |
| Micrococcus luteus IFO 12708 | 0.02≧ | 0.02≧ | 0.02≧ | 0.08 | 0.16 | 0.04 |
| Bacillus subtilis IFO 3134 | 0.02≧ | 0.02≧ | 0.02≧ | 0.08 | 0.16 | 0.08 |
| Staphylococcus aureus IFO 12732 | 0.02≧ | 0.02≧ | 0.02≧ | 0.04 | 0.04 | 0.02≧ |
| Escherichia coli IFO 12734 | 5 | 5 | >10 | >10 | >10 | >10 |
| Klebsiella pneumoniae IFO 3512 | 2.5 | 5 | >10 | >10 | >10 | >10 |
| Mycobacterium smegmatis ATCC 607 | 0.63 | 1.25 | 0.63 | 1.25 | 1.25 | 1.25 |

| Test organism | Minimal inhibitory concentration (μg/ml) | | | | |
|---|---|---|---|---|---|
| | Derivative No. 12 | Derivative No. 13 | Derivative No. 14 | Derivative No. 15 | Derivative No. 16 |
| Micrococcus luteus IFO 12708 | 0.02≧ | 0.16 | 0.31 | 0.04 | 0.02≧ |
| Bacillus subtilis IFO 3134 | 0.02≧ | 0.16 | 0.08 | 0.08 | 0.02≧ |
| Staphylococcus aureus IFO 12732 | 0.02≧ | 0.04 | 0.08 | 0.04 | 0.02≧ |
| Escherichia coli IFO 12734 | 5 | >10 | >10 | >10 | 5 |
| Klebsiella pneumoniae IFO 3512 | 5 | >10 | >10 | >10 | 5 |
| Mycobacterium smegmatis ATCC 607 | 1.25 | 1.25 | 0.63 | 1.25 | 1.25 |

| Test organism | Minimal inhibitory concentration (μg/ml) | |
|---|---|---|
| | Derivative No. 17 | Rifampicin |
| Micrococcus luteus IFO 12708 | 0.08 | 0.02≧ |
| Bacillus subtilis IFO 3134 | 0.04 | 0.08 |
| Staphylococcus aureus IFO 12732 | 0.02≧ | 0.02≧ |

TABLE 2-continued

| | | |
|---|---|---|
| Escherichia coli IFO 12734 | >10 | >10 |
| Klebsiella pneumoniae IFO 3512 | >10 | 5 |
| Mycobacterium smegmatis ATCC 607 | 1.25 | 10 |

The rifamycin derivative (I) of the present invention also exhibits a strong antibacterial activity against tubercle bacilli.

The antibacterial activity of the ribamycin derivative (I) against a tubercle bacillus was determined as follows: A tubercle bacillus, *Mycobacterium tuberculosis* $H_{37}Rv$, was cultivated in the Dubos medium to prepare a suspension containing the bacterium in a concentration of 1 mg/ml. The suspension was diluted ten times with sterile distilled water and 0.05 ml of the dilution was inoculated into 2 ml of the Kirchner liquid medium containing 10% by volume of bovine serum. The evaluation of the antibacterial activity was carried out in a usual manner. Each test compound was diluted with the Kirchner liquid medium containing 10% by volume of bovine serum by a two-fold series. Then, the above-mentioned medium containing the bacterium was added to each of the dilutions of the test compound. After each medium was cultured at 37° C. for 4 weeks, the growth of the test bacteria was observed by the naked eye. The minimum concentration of the test compound, at which the growth of the test bacterium was completely inhibited, was taken as minimal inhibitory concentration.

The results are shown in Tables 3 and 4. From the results shown in Tables 3 and 4, it is confirmed that the rifamycin derivative (I) of the present invention exhibits a strong antibacterial activity against tubercle bacilli. Derivative No. in Tables 3 and 4 corresponds to derivative No. in Table 1.

TABLE 3

| Derivative No. | Minimal inhibitory concentration ($\mu$g/ml) |
|---|---|
| 1 | 0.017 |
| 2 | 0.15 |
| 3 | 0.017 |
| 4 | 0.017 |
| 5 | 0.035 |
| 7 | 0.017 |
| 8 | 0.07 |
| 9 | 0.035 |
| 10 | 0.07 |
| 11 | 0.017 |
| 12 | 0.017 |
| 13 | 0.07 |
| 15 | 0.008 |
| 17 | 0.07 |
| Refampicin | 0.6 |

TABLE 4

| Derivative No. | Minimal inhibitory concentration ($\mu$g/ml) |
|---|---|
| 6 | 0.008 |
| Rifampicin | 0.3 |

The rifamycin derivative (I) of the present invention is easily absorbed on oral administration to give a high blood level.

The derivatives No. 4 and No. 11 shown in Table 1 were orally administered to ddY male mice (7 weeks), respectively, in a dose of 20 mg/kg. The concentration of the test compound in the plasma was measured by a bioassay method employing *Micrococcus luteus* IFO 12708 as an assay bacterium according to a usual manner. The results are as follows: As for the derivative No. 4, the concentrations in the plasma after 1 hour, 3 hours, 5 hours and 8 hours from the administration were 17.0 $\mu$g/ml, 13.3 $\mu$g/ml, 14.5 $\mu$g/ml, 4.2 $\mu$g/ml, respectively. As for the derivative No. 11, the concentrations in the plasma after 1 hour, 3 hours, 5 hours and 8 hours from the administration were 17.3 $\mu$g/ml, 16.2 $\mu$g/ml, 13.8 $\mu$g/ml and 10.1 $\mu$g/ml, respectively.

The rifamycin derivative (I) of the invention exhibits an excellent effect on a treatment of mice experimentally suffering from tuberculosis.

A test for examining the therapeutic effect of the rifamycin derivative (I) on tuberculosis using mice are shown below.

Groups of 20 ddY male mice (5 weeks) were employed. A tubercle bacillus, *Mycobacterium tuberculosis* $H_{37}Rv$ was cultivated in the Dubos medium to obtain a concentrated suspension of the bacterium and 0.2 ml of the suspension (viable count: $2.4 \times 10^8$) was inoculated into the caudal vein of the mice to make them being infected with tuberculosis. There was prepared a suspension of each test compound in a 2.5% by weight aqueous solution of gum arabic containing 0.2% by weight Tween 80. The treatment was started on the next day of the infection. The suspension of the test compound was orally administered to the mice in a dose of 0.2 ml, i.e. 200 $\mu$g/mouse. As a control, a 2.5% by weight aqueous solution of gum arabic containing 0.2% by weight of Tween 80 which did not contain any test compound was administered to mice. The treatment was conducted once a day and six days a week. The therapeutic effect was evaluated on the basis of prolonged life of the mice being infected with tuberculosis.

The results are shown in FIG. 1. In FIG. 1, the point, a, means the time that mice were infected, and the point, b, means the time that the treatment started. From the results shown in FIG. 1, in the treatment using the derivative No. 8 of the invention, there was not observed any dead mouse for 38 days from the beginning of the treatment. Accordingly, it is apparent that the derivative No. 8 exhibits an excellent therapeutic effect as compared with rifampicin as a comparative medicine and the derivative A disclosed in U.S. Pat. No. 4,690,919 having the formula mentioned below. On the other hand, as for the derivative B disclosed in U.S. Pat. No. 4,690,915, having the formula mentioned below, and the derivative C disclosed in EP No. 0253340, having the formula mentioned below, it is confirmed that they are inferior to rifampicin in their therapeutic effect in a therapeutic test.

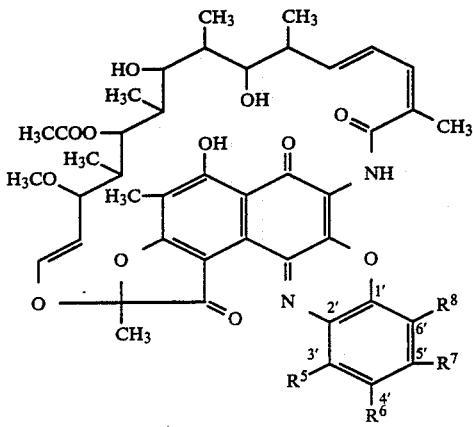

Derivative A: $R^5$: —OH, $R^6$ and $R^8$: —H, and $R^7$:

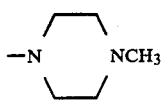

Derivative B: $R^5$, $R^6$ and $R^8$: —H, and $R^7$:

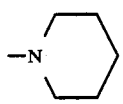

Derivative C: $R^5$ and $R^6$: —H, $R^7$:

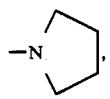, and $R^8$: —$C_2H_5$

Further, the above-mentioned test for treatment of mice being infected with tuberculosis was repeated except that groups of 10 ddY male mice were used to determine the survival rate of the mice on the fortieth day after the beginning of the test. The results are shown in Table 5.

TABLE 5

| Test compound | Survival rate (%) |
|---|---|
| Control (not given) | 30 |
| Derivative No. 4 | 100 |
| Derivative No. 13 | 100 |
| Derivative No. 17 | 100 |
| Rifampicin | 80 |

As for the groups which were given the derivative No. 4, No. 13 or No. 17 of the invention, there was not observed any dead mouse. On the other hand, the survival rate of the control group which was not given any medicine was 30%, and the survival rate of the group which was given rifampicin was 80%. The results show that the rifamycin derivative (I) of the invention is very effective as a drug for tuberculosis.

Further the rifamycin derivatives shown in Table 1 did not show any toxicity when they were orally administered in a dose of 1,000 mg/kg to mice. There results reveal that the rifamycin derivative (I) of the present invention has a low texicity.

Antibacterial agents containing the rifamycin derivative (I) as an effective ingredient may be in any preparation form for oral, or rectal or other parenteral administration. Examples of the preparation form are, for instance, tablets, capsules, granules, syrups, suppositories, ointments, and the like. Carriers used for the preparations of the antibacterial agent of the present invention are organic or inorganic pharmaceutical carriers in either solid or liquid state, which are inactive under usual conditions, suitable for oral, or rectal or other parenteral administration. Examples of the carrier include crystalline cellulose, gelatin, lactose, starch, magnesium stearate, talc, vegetable or animal fats or oils, gums and polyalkylene glycol. The content of the rifamycin derivative (I) in the preparation varies from 0.2 to 100% by weight. The antibacterial agent of the present invention can contain another pharmaceutical ingredient such as another antibacterial agent compatible with the rifamycin derivative (I). In this case, the rifamycin derivative (I) is not necessarily a main ingredient of the preparation.

The antibacterial agent of the present invention is administered in such a dose that the desired activity is achieved without any side-effect. Though the actual dose should be determined according to the judgement of the doctor, a usual dosage is about 10 mg to about 10 g, preferably about 20 mg to about 5 g, on the basis of the rifamycin derivative (I) per day for adults. The antibacterial agent of the present invention can be used in a pharmaceutical dosage unit containing 1 mg to 5 g, preferably 3 mg to 1 g of an effective component.

The present invention is more specifically described and explained by the following Examples. However, it should be understood that the present invention is not limited to such Examples and various changes and modifications can be made without departing from the scope and spirit of the present invention.

In Examples, derivative No. corresponds to derivative No. in Table 1. The mixing ratio of solvents as an eluent used in column chromatography or as a developer used in thin layer chromatography was represented in terms of volume ratio (v/v).

EXAMPLE 1

[Synthesis of 6'-methoxybenzoxazinorifamycin]

To a stirred mixture of 50 ml of water, 150 ml of ether and 15.0 g of 2-methoxyphenol was added dropwise 12.7 ml of 61% nitric acid, and the mixture was stirred at room temperature for 15 minutes. The ether layer was separated from the aqueous layer and dried over anhydrous sodium sulfate. After the drying agent was filtered off, the solvent was distilled off under reduced pressure. The residue was purified by silica-gel column-chromatography using Wakogel ® C-200 [eluent: chloroform-n-hexane (1:1)] to give 4.72 g of 2-methoxy-6-nitrophenol.

To a suspension of 4.72 g of 2-methoxy 6-nitrophenol in a mixture of 100 ml of water and 30 ml of methanol was added 29.3 g of sodium dithionite. The mixture was stirred at 60° C. until it became a uniform and colorless solution. To the reaction mixture was added a saturated aqueous solution of sodium chloride. The mixture was extracted with ethyl acetate and dried over anhydrous sodium sulfate. After the drying agent was filtered off, the solvent was distilled off under reduced pressure to give 3.65 g of crude 2-amino-6-methoxyphenol.

A solution of 18.65 g of rifamycin S and 3.65 g of the crude 2-amino-6-methoxyphenol in 400 ml of toluene was stirred at room temperature for 12 days. After insoluble substances were filtered off, the solvent was distilled off under reduced pressure, and the residue was dissolved in 300 ml of ethanol. To the solution was added 9.0 g of manganese dioxide and the mixture was stirred at room temperature for 7 hours. Manganese dioxide was filtered off by using a filter aid and the solvent was distilled away under reduced pressure. The residue was purified by silica-gel column-chromatography employing Wakogel® C-200 [eluent: chloroform-methanol (99:1)] to give 10.15 g of 6'-methoxybenzoxazinorifamycin. Thin layer chromatography:
Rf=0.21, dark brown spot [carrier: silica-gel, developer: chloroform-acetone (9:1)]

EXAMPLE 2

[Synthesis of derivative No. 1]

To a solution of 8.0 g of 6'-methoxybenzoxazinorifamycin, which was synthesized in the same manner as in Example 1, in 30 ml of dimethyl sulfoxide were added 0.46 ml of pyrrolidine and 1.5 g of manganese dioxide, and the mixture was stirred at room temperature for 5 days. The reaction mixture was diluted by addition of ethyl acetate and insoluble substances were filtered off. Then, the filtrate was washed successively with water and with a saturated aqueous solution of sodium chloride, and dried over anhydrous sodium sulfate. After the drying agent was filtered off, the solvent was distilled off under reduced pressure. The residue was purified twice by silica-gel column-chromatography employing Wakogel® C-200 [eluent: ethyl acetate for the first purification and chloroform-methanol (99:1) for the second purification] and the product was crystallized from a mixture of ethyl acetate and n-hexane to give 0.42 g of the derivative No. 1.

EXAMPLE 3

[Synthesis of derivative No. 2]

To a solution of 6.49 g of 6'-methoxybenzoxazinorifamycin, which was synthesized in the same manner as in Example 1, in 60 ml of dimethyl sulfoxide were added 1.77 ml of N-methylpiperazine and 3.0 g of manganese dioxide, and the mixture was stirred at room temperature for twenty-four hours. The reaction mixture was treated in the same manner as in Example 2 and the residue was purified twice by silica-gel column-chromatography [eluent: chloroform-methanol (95:5)] and crystallized from a mixture of ethyl acetate and n-hexane, giving 0.56 g of the derivative No. 2.

EXAMPLE 4

[Synthesis of derivative No. 3]

To a solution of 5.0 g of 6'-methoxybenzoxazinorifamycin, which was synthesized in the same manner as in Example 1, in 50 ml of dimethyl sulfoxide were added 1.05 g of N-isobutylpiperazine and 2.5 g of manganese dioxide, and the mixture was stirred at room temperature for 4 days. The reaction mixture was treated, purified and crystallized in the same manner as in Example 2 to give 0.70 g of the derivative No. 3.

EXAMPLE 5

[Synthesis of 6'-ethoxybenzoxazinorifamycin]

In the same manner as in Example 1, 25.8 g of 2-ethoxyphenol was nitrated and the resulting nitro compound was reduced to give 10.9 g of crude 2-amino-6-ethoxyphenol.

A solution of 49.5 g of rifamycin S and 10.9 g of the crude 2-amino-6-ethoxyphenol in 1 l of toluene was stirred at room temperature for 18 days. After insoluble substances were filtered off, the solvent was distilled off under reduced pressure. After the residue was dissolved in 300 ml of ethanol, 15.0 g of manganese dioxide was added thereto, and the mixture was stirred at room temperature for twenty-four hours. Manganese dioxide was filtered off by using a filter aid and the solvent was distilled away under reduced pressure. The residue was purified by silica-gel column-chromatography [eluent: chloroform-methanol (99:1)], and the resultant was crystallized from a mixture of ethyl acetate and n-hexane to give 35.6 g of 6'-ethoxybenzoxazinorifamycin. Thin layer chromatography:
Rf=0.52, dark brown spot [carrier: silica-gel, developer: chloroform-acetone (7:3)]

EXAMPLE 6

[Synthesis of derivative No. 4]

To a solution of 3.24 g of 6'-ethoxybenzoxazinorifamycin obtained in Example 5 in 30 ml of dimethyl sulfoxide were added 0.65 ml of pyrrolidine and 1.5 g of manganese dioxide, and the mixture was stirred at room temperature for twenty-four hours. The reaction mixture was treated in the same manner as in Example 2 to give 0.89 g of the derivative No. 4.

EXAMPLE 7

[Synthesis of derivative No. 5]

To a solution of 3.0 g of 6'-ethoxybenzoxazinorifamycin obtained in Example 5 in 30 ml of dimethyl sulfoxide were added 0.48 ml of N-methylpiperazine and 1.5 g of manganese dioxide, and the mixture was stirred at room temperature for twenty-four hours. The reaction mixture was treated, purified and crystallized in the same manner as in Example 3 to give 0.51 g of the derivative No. 5.

EXAMPLE 8

[Synthesis of derivative No. 6]

To a solution of 5.0 g of 6'-ethoxybenzoxazinorifamycin obtained in Example 5 in 50 ml of dimethyl sulfoxide were added 0.84 ml of N-ethylpiperazine and 2.5 g of manganese dioxide, and the mixture was stirred at room temperature for twenty-four hours. The reaction mixture was treated in the same manner as in Example 2 and the resulting residue was purified twice by silica-gel column-chromatography [eluent: chloroform-methanol (98:2)] and crystallized from a mixture of ethyl acetate and n-hexane to give 1.40 g of the derivative No. 6.

EXAMPLE 9

[Synthesis of derivative No. 7]

To a solution of 4.0 g of 6'-ethoxybenzoxazinorifamycin obtained in Example 5 in 40 ml of dimethyl sulfoxide were added 0.72 g of N-isobutylpiperazine and 2.0 g of manganese dioxide, and the mixture was stirred at room temperature for 6 days. The reaction mixture was treated in the same manner as in Example 2 and the resulting residue was purified three times by silica-gel column-chromatography [eluent: chloroform-methanol (97:3 by volume)] and crystallized from a mixture of ethyl acetate and n-hexane to give 0.17 g of the derivative No. 7.

EXAMPLE 10

[Synthesis of derivative No. 8]

To a solution of 5.0 g of 6'-ethoxybenzoxazinorifamycin obtained in Example 5 in 50 ml of dimethyl sulfoxide were added 1.0 g of N-isobutylpiperazine and 2.5 g of manganese dioxide, and the mixture was stirred at room temperature for 3 hours. The reaction mixture was treated in the same manner as in Example 2 to give 0.74 g of the derivative No. 8.

EXAMPLE 11

[Synthesis of 6'-n-propoxybenzoxazinorifamycin]

In the same manner as in Example 1, 20.0 g of 2-n-propoxyphenol was nitrated and the resulting nitro compound was reduced to give 10.6 g of crude 2-amino-6-n-propoxyphenol.

A solution of 44.2 g of rifamycin S and 10.6 g of the crude 2-amino-6-n-propoxyphenol in 800 ml of toluene was stirred at room temperature for 12 days. After insoluble substances were filtered off, the solvent was distilled off under reduced pressure. After the residue was dissolved in 500 ml of ethanol, 20.0 g of manganese dioxide was added thereto, and the mixture was stirred at room temperature for twenty-four hours. Manganese dioxide was filtered off by using a filter aid and the solvent was distilled away under reduced pressure. The residue was purified by silica-gel column-chromatography [eluent: chloroform-methanol (99:1)], and the resultant was crystallized from a mixture of ethyl acetate and n-hexane to give 22.1 g of 6'-n-propoxybenzoxazinorifamycin. Thin layer chromatography:
Rf=0.50, dark red spot [carrier: silica gel, developer: chloroform-acetone (7:3)]

EXAMPLE 12

[Synthesis of derivative No. 9]

To a solution of 5.0 g of 6'-n-propoxybenzoxazinorifamycin obtained in Example 11 in 50 ml of dimethyl sulfoxide were added 0.74 ml of pyrrolidine and 2.5 g of manganese dioxide, and the mixture was stirred at room temperature for 3 days. The reaction mixture was treated, purified and crystallized in the same manner as in Example 2 to give 1.19 g of the derivative No. 9.

EXAMPLE 13

[Synthesis of derivative No. 10]

To a solution of 5.0 g of 6'-n-propoxybenzoxazinorifamycin obtained in Example 11 in 50 ml of dimethyl sulfoxide were added 1.01 g of N-isobutylpiperazine and 2.5 g of manganese dioxide, and the mixture was stirred at room temperature for twenty-four hours. The reaction mixture was treated, purified and crystallized in the same manner as in Example 2 to give 0.97 g of the derivative No. 10.

EXAMPLE 14

[Synthesis of 6'-isopropoxybenzoxazinorifamycin]

In the same manner as in Example 1, 24.8 g of 2-isopropoxyphenol was nitrated and the resulting nitro compound was reduced to give 16.0 g of crude 2-amino-6-isopropoxyphenol.

A solution of 66.7 g of rifamycin S and 16.0 g of the crude 2-amino-6-isopropoxyphenol in 1 l of toluene was stirred at room temperature for 13 days. After insoluble substances were filtered off, the solvent was distilled off under reduced pressure. After the residue was dissolved in 700 ml of ethanol, 30 g of manganese dioxide was added thereto, and the mixture was stirred at room temperature for twenty-four hours. Manganese dioxide was filtered off by using a filter aid and the solvent was distilled away under reduced pressure. The residue was purified by silica-gel column-chromatography twice [eluent: chloroform-methanol (99:1)] to give 25.9 g of 6'-isopropoxybenzoxazinorifamycin. Thin layer chromatography:
Rf=0.49, dark brown spot [carrier: silica-gel, developer: chloroform-acetone (7:3)]

EXAMPLE 15

[Synthesis of derivative No. 11]

To a solution of 5.0 g of 6'-isopropoxybenzoxazinorifamycin obtained in Example 14 in 50 ml of dimethyl sulfoxide were added 0.59 ml of pyrrolidine and 2.5 g of manganese dioxide, and the mixture was stirred at room temperature for twenty-four hours. The reaction mixture was treated, purified and crystallized in the same manner as in Example 2 to give 1.68 g of the derivative No. 11.

EXAMPLE 16

[Synthesis of derivative No. 12]

To a solution of 5.0 g of 6'-isopropoxybenzoxazinorifamycin obtained in Example 14 in 50 ml of dimethyl sulfoxide were added 0.90 ml of N-ethylpiperazine and 2.5 g of manganese dioxide, and the mixture was stirred at room temperature for 2 days. The reaction mixture was treated, purified and crystallized in the same manner as in Example 9 to give 1.57 g of the derivative No. 12.

EXAMPLE 17

[Synthesis of derivative No. 13]

To a solution of 5.0 g of 6'-isopropoxybenzoxazinorifamycin obtained in Example 14 in 50 ml of dimethyl sulfoxide were added 1.01 g of N-isobutylpiperazine and 2.5 g of manganese dioxide, and the mixture was stirred at room temperature for 7 hours. The reaction mixture was treated, purified and crystallized in the same manner as in Example 2 to give 1.29 g of the derivative No. 13.

EXAMPLE 18

[Synthesis of 6'-isobutoxybenzoxazinorifamycin]

In the same manner as in Example 1, 20.0 g of 2-isobutoxyphenol was nitrated and the resulting nitro compound was reduced to give 7.5 g of crude 2-amino-6isobutoxyphenol.

A solution of 29.3 g of rifamycin S and 7.5 g of the crude 2-amino-6-isobutoxyphenol in 600 ml of toluene was stirred at room temperature of 7 days. After insoluble substances were filtered off, the solvent was distilled off under reduced pressure. After the residue was dissolved in 300 ml of ethanol, 15.0 g of manganese dioxide was added thereto, and the mixture was stirred at room temperature for twenty-four hours. Manganese dioxide was filtered off by using a filter aid and the solvent was distilled away under reduced pressure. The residue was purified by silica-gel column-chromatography [eluent: chloroform-methanol (99:1)] to give 9.88 g of 6'-isobutoxybenzoxazinorifamycin. Thin layer chromatography:

Rf=0.59, dark red spot [carrier: silica-gel, developer: ethyl acetate]

EXAMPLE 19

[Synthesis of derivative No. 14]

To a solution of 5.0 g of 6'-isobutoxybenzoxazinorifamycin obtained in Example 18 in 50 ml of dimethyl sulfoxide were added 1.0 g of N-isobutylpiperazine and 2.5 g of manganese dioxide, and the mixture was stirred at room temperature for 2 days. The reaction mixture was treated, purified and crystallized in the same manner as in Example 2 to give 0.84 g of the derivative No. 14.

EXAMPLE 20

[Synthesis of 6'-methoxy-3'-methylbenzoxazinorifamycin]

In the same manner as in Example 1, 10.0 g of 2-methoxy-5-methylphenol was nitrated, and the resulting nitro compound was reduced to give 2.6 g of crude 2-amino-3-methyl-6-methoxyphenol.

A solution of 11.8 g of rifamycin S and 2.6 g of the crude 2-amino-3-methyl-6-methoxyphenol in 250 ml of toluene was stirred at room temperature for 14 days. After insoluble substances were filtered off, the solvent was distilled off under reduced pressure. After the residue was dissolved in 250 ml of ethanol, 6.0 g of manganese dioxide was added thereto, and the mixture was stirred at room temperature for 1 hour. Manganese dioxide was filtered off by using a filter aid and the solvent was distilled away under reduced pressure. The residue was purified by silica-gel column-chromatography [eluent: chloroform-methanol (99:1)] to give 6.3 g of 6'-methoxy-3'-methylbenzoxazinorifamycin. Thin layer chromatography:

Rf=0.50, dark brown spot [carrier: silica-gel, developer: chloroform-acetone (7:3)]

EXAMPLE 21

[Synthesis of derivative No. 15]

To a solution of 3.0 g of 6'-methoxy-3'-methylbenzoxazinorifamycin obtained in Example 20 in 30 ml of dimethyl sulfoxide were added 0.6 ml of pyrrolidine and 1.5 g of manganese dioxide, and the mixture was stirred at room temperature for 5.5 hours. The reaction mixture was treated, purified and crystallized in the same manner as in Example 2 to give 0.56 g of the derivative No. 15.

EXAMPLE 22

[Synthesis of derivative No. 16]

To a solution of 3.0 g of 6'-methoxy-3'-methylbenzoxazinorifamycin obtained in Example 20 in 30 ml of dimethyl sulfoxide were added 0.80 ml of N-methylpiperazine and 1.5 g of manganese dioxide, and the mixture was stirred at room temperature for 7 hours. The reaction mixture was treated, purified and crystallized in the same manner as in Example 3 to give 1.21 g of the derivative No. 16.

EXAMPLE 23

[Synthesis of derivative No. 17]

To a solution of 4.0 g of 6'-methoxy-3'-methylbenzoxazinorifamycin obtained in Example 20 in 40 ml of dimethyl sulfoxide were added 1.37 g of N-isobutylpiperazine and 2.0 g of manganese dioxide, and the mixture was stirred at room temperature for 6 hours. The reaction mixture was treated, purified and crystallized in the same manner as in Example 2 to give 2.37 g of the derivative No. 17.

In addition to the ingredients used in the Examples, other ingredients can be used in the Examples as set forth in the specification to obtain substantially the same results.

What we claim is:

1. A rifamycin derivative having the formula (I):

[Chemical structure of formula (I)]

wherein $R^1$ is hydrogen atom, methyl group or ethyl group, $R^2$ is an alkyl group having 1 to 4 carbon atoms, and A is a group having the formula:

[Structure: $-N$ with $(CH_2)_n$ ring]

in which n is an integer of 3 to 5, or a group having the formula:

[Structure: piperazine ring with $-N$ and $NR^3$]

in which $R^3$ is an alkyl group having 1 to 5 carbon atoms; or a salt thereof.

2. The rifamycin derivative or a salt thereof of claim 1, wherein, in the formula (I), $R^1$ is hydrogen atom or methyl group, $R^2$ is an alkyl group having 1 to 3 carbon atoms, and A is a group having the formula:

[Structure: $-N$ with ring]

or a group having the formula:

in which R³ is an alkyl group having 3 to 5 carbon atoms.

3. The rifamycin derivative or a salt thereof of claim 1, wherein, in the formula (I), R¹ is hydrogen atom, R² is ethyl group, and A is a group having the formula:

4. The rifamycin derivative or a salt thereof of claim 1, wherein, in the formula (I), R¹ is hydrogen atom, R² is ethyl group, and A is a group having the formula:

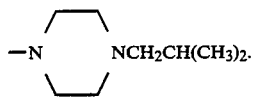

5. The rifamycin derivative or a salt thereof of claim 1, wherein, in the formula (I), R¹ is hydrogen atom, R² is isopropyl group, and A is a group having the formula:

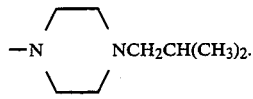

6. The rifamycin derivative or a salt thereof of claim 1, wherein, in the formula (I), R¹ is methyl group, R² is methyl group, and A is a group having the formula:

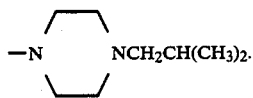

7. An antibacterial composition comprising an inert pharmaceutical carrier and a rifamycin derivative having the formula (I):

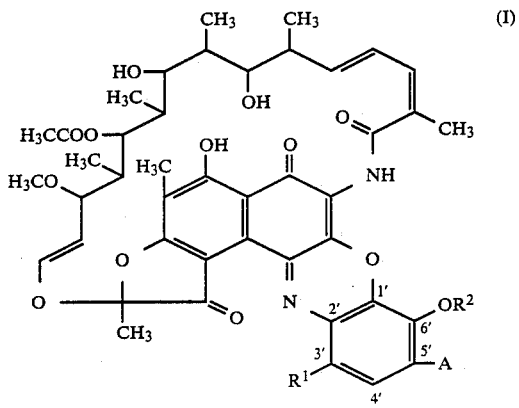

wherein R¹ is hydrogen atom, methyl group or ethyl group, R² is an alkyl group having 1 to 4 carbon atoms, and A is a group having the formula:

in which n is an integer of 3 to 5, or a group having the formula:

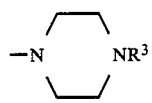

in which R³ is an alkyl group having 1 to 5 carbon atoms; or a pharmacologically acceptable salt thereof.

* * * * *